US007402558B2

(12) United States Patent
Menezo

(10) Patent No.: US 7,402,558 B2
(45) Date of Patent: *Jul. 22, 2008

(54) METHOD FOR AIDING IMPLANTATION OR DECREASING MISCARRIAGE RATE

(75) Inventor: Yves Menezo, Clauire (FR)

(73) Assignee: Laboratoires Seronosa, Coinsins, Vaud (CH)

( * ) Notice: Subject to any disclaimer, the term of this patent is extended or adjusted under 35 U.S.C. 154(b) by 334 days.

This patent is subject to a terminal disclaimer.

(21) Appl. No.: 10/489,412

(22) PCT Filed: Sep. 12, 2002

(86) PCT No.: PCT/GB02/04167

§ 371 (c)(1),
(2), (4) Date: Sep. 14, 2004

(87) PCT Pub. No.: WO03/022303

PCT Pub. Date: Mar. 20, 2003

(65) Prior Publication Data

US 2005/0020489 A1    Jan. 27, 2005

(30) Foreign Application Priority Data

Sep. 12, 2001    (EP)    .................... 01307758

(51) Int. Cl.
*A61K 38/08*    (2006.01)
*A61K 38/09*    (2006.01)
*A61K 38/18*    (2006.01)
*A61K 38/19*    (2006.01)
*A61K 38/24*    (2006.01)
*C07K 14/475*    (2006.01)

(52) U.S. Cl. .................... 514/2; 514/8; 514/12; 514/15; 514/16; 424/85.1; 530/350; 530/351; 930/110; 930/130

(58) Field of Classification Search ........................ None
See application file for complete search history.

(56) References Cited

U.S. PATENT DOCUMENTS

| 5,705,478 | A | 1/1998 | Boime | |
|---|---|---|---|---|
| 6,407,057 | B1* | 6/2002 | Emperaire | ..................... 514/2 |
| 6,653,286 | B1* | 11/2003 | Mannaerts et al. | ............ 514/15 |
| 2002/0103106 | A1* | 8/2002 | Palmer et al. | .................. 514/1 |

FOREIGN PATENT DOCUMENTS

| EP | 0 170 502 | 6/1991 |
|---|---|---|
| WO | WO-99/13081 | 3/1999 |
| WO | WO-00/50066 | 8/2000 |
| WO | WO-00/67778 | 11/2000 |
| WO | WO-01/54715 | 8/2001 |

OTHER PUBLICATIONS

Warne et al, The International Recombinant Human Chorionic Gonadotropin Study Group, Induction of Ovulation in WOrld Health Organization group II anovulatory women undergoing follicular stimulation with recombinant human follicle-stimulating hormone: a comparison of rhCG and urinary hCG, Fertility and Sterility, Jun. 2001, 75(6): 1111-1118.*
Sullivan MW, Stewart-Akers A, Krasnow JS, Berga SL and Zeleznik AJ, Ovarian Response in Women to Recombinant Follicle-Stimulating Hormone and Luteinizing Hormone (LH): A Role for LH in the FInal Stages of Follicular Maturation, The Journal of Clinical Endocrinology and Metabolism, 1999, 84(1): 228-232.*
David Lindsay Healy et al, "Female Infertility: Causes and Treatment", The Lancet, Jun. 18, 1994, vol. 343, pp. 1539-1544.
Marco Filicori, "Gonadotropin-Releasing Hormone Analogs in Ovulation Induction: Current Status and Perspectives", Journal of Clinical Endocrinology and Metabolism, 1996, vol. 81, pp. 2413-2416.
Marco Filicori et al, "Different Gonadotropin and Leuprorelin Ovulation Induction Regimens Markedly Affect Follicular Fluid Hormone Levels and Folliculogenesis", Fertility and Sterility, Feb. 1996, vol. 65, pp. 387-393.
Stephen G. Hillier et al, "Gonadotrophin Control of Follicular Function", Hrm Res, 1995, vol. 43, pp. 216-223.
Melissa A. Esposito et al, "Role of Periovulatory Luteinizing Hormone Concentrations During Assisted Reproductive . . . ", Fertility and Sterility, Mar. 2001, vol. 75, pp. 519-524.
"Recombinant Human Luteinizing Hormone (LH) to Support Recombinant Human Follicle-Stimulating Hormone (FSH)-Induced Follicular . . . ", Journal of Clinical Endocrinology and Metabolism, 1998, vol. 83, pp. 1507-1514.
M. Filicori et al, "Luteinizing Hormone Activity Supplementation Enhances Follicle-Stimulating Hormone Efficacy and Improves Ovulation Induction Outcome", The Journal of Clinical Endocrinology and Metabolism, 1999, vol. 84, pp. 2659-2663.
Ioannis E. Messinis, M.D. et al, "The Importance of Human Chorionic Gonadotropin Support of the Corpus Luteum During Human Gonadotropin Therapy in Women with Anovulatory Infertility", Fertility and Sterility, vol. 50, pp. 31-35.
Z.M. Lei et al, "The Expression of Human Chorionic Gonadotropin/Luteinizing Hormone Receptors in Human Endometrial and Myometrial Blood Vessels", 1992, vol. 75, pp. 651-659.
Hugh P. J. Bennett et al, "Peptide Hormones and Their Analogues: Distribution, Clearance from the Circulation, and Inactivation in Vivo", Pharmacological Reviews, 1979, vol. 30, pp. 247-292.
B.M.J.L. Mannaerts et al, "A Randomized Three-Way Cross-Over Study in Healthy Pituitary-Suppressed Women to Compare the Bioavailability of Human Chorionic Gonadotrophin . . . ", Human Reproduction, 1998, vol. 13, pp. 1461-1464.
Wiebe Olijve et al, "Molecular Biology and Biochemistry of Human Recombinant Follicle Stimulating Hormone (Puregon)", Molecular Human Reproduction, 1996, vol. 2, pp. 371-382.
Tadashi Sugahara et al, "Biosynthesis of a Biologically Active Single Peptide Chain Containing the Human Common α and Chorionic Gonadotropin β Subunits in Tandem", Medical Sciences, 1995, vol. 92, pp. 2041-2045.

(Continued)

*Primary Examiner*—Anish Gupta
*Assistant Examiner*—Julie Ha
(74) *Attorney, Agent, or Firm*—Browdy and Neimark, PLLC

(57) ABSTRACT

The invention provides a protocol leading to improved embryo implantation rates and/or decreased miscarriage rates in which hCG or LH, or a bio-analogue thereof, is administered during the follicular phase.

6 Claims, No Drawings

OTHER PUBLICATIONS

Judith L. Vaitukaitis et al, "A Radioimmunoassay Which Specifically Measures Human Chorionic Gonadotropin in the Presence of Human Luteinizing Hormone", Am. J. Obstet., Gynecol., Jul. 15, 1972, vol. 113, pp. 751-758.

"Radioimmunoassay of Human Choriogonadotropin", Clinical Chemistry, 1985, col. 31, pp. 1749-1754.

Lee Tyrey, "Human Chorionic Gonadotropin Assays and Their Uses", Obstetrics and Gynecology Clinics of North America, Sep. 1988, vol. 15, pp. 457-475.

Michael W. Sullivan et al, "Ovarian Responses in Women to Recombinant Follicle-Stimulating Hormone and Luteinizing Hormone (LH): A Role for LH in the Final Stages of Follicular Maturation", Journal of Clinical Endocrinology and Metabolism, 1999, vol. 84, pp. 228-232.

E. Kousta et al, "Successful Induction of Ovulation and Completed Pregnancy Using Recombinant Human Luteinizing hormone and Follicle Stimulating Hormone in a Woman with Kallmann's Syndrome", Human Reproduction, 1996, vol. 11, pp. 70-71.

Kimberly A. Thompson et al, "Gonadotropin Requirements of the Developing Follicle", Fertility and Sterility, 1995, vol. 63, pp. 273-276.

Uma Deve Gordon et al, "A Randomized Prospective Assessor-Blind Evaluation of Luteinizing Hormone Dosage and In Vitro Fertilization Outcome", Fertility and Sterility, Feb. 2001, vol. 75, pp. 324-331.

Zeev Blumenfeld et al, "Early Pregnancy Wastage: The Role of Repetitive Human Chorionic Gonadotropin Supplementation During the First 8 Weeks of Gestation", Fertility and Sterility, Jul. 1992, vol. 58, pp. 19-23.

M. Filicori et al, "Luteinizing Hormone Activity Supplementation Enhances Follicle-Stimulating Hormone Efficacy and Improves Ovulation Induction Outcome", The Journal of Endocrinology and Metabolism, 1999, vol. 84, pp. 2659-2663.

W.R. Robertson et al, "the In Vitro bioassay of Peptide Hormones", Peptide Hormones: a Practical Approach, IRL Press, Oxford, 1990, pp. 121-159.

* cited by examiner

METHOD FOR AIDING IMPLANTATION OR DECREASING MISCARRIAGE RATE

FIELD OF INVENTION

The invention relates to the field of in vivo and in vitro assisted reproduction technologies (ART), specifically controlled ovarian hyperstimulation (COH) using gonadotropins.

BACKGROUND OF THE INVENTION

Treatment of infertility by assisted reproduction technologies (ART) such as in vitro fertilisation (IVF) or IVF in conjunction with intracytoplasmic sperm injection. (IVF/ICSI) and embryo transfer (ET) requires controlled ovarian hyperstimulation (COH) to increase the number of oocytes[1]. Standard regimens[2] for COH include a down-regulation phase in which endogenous luteinising hormone (LH) is suppressed by administration of a gonadotropin releasing hormone (GnRH) agonist followed by a stimulation phase in which follicular development (folliculogenesis) is induced by daily administration of follicle stimulating hormone (FSH), usually at about 150 IU/day. Other molecules having FSH activity may also be used. Alternatively stimulation is started after spontaneous or induced menstruation while preventing the occurrence of an LH surge by administration of a GnRH-antagonist, usually starting on about day 6 or 7 of FSH administration. In superovulation protocols for ART, multiple follicular development is the desired aim. When there are at least 3 follicles >16 mm (one of 18 mm), a single bolus of hCG (5-10,000 IU) is given to trigger ovulation. Oocyte recovery is timed for 36-38 hours after the hCG injection.

The rationale for the use of GnRH agonists and antagonists in this context is the prevention of an untimely LH surge that would cause premature ovulation and follicle luteinisation[3]. GnRH agonist regimens have become the accepted norm in the clinic. It has been found that long regimens (i.e., those started in the midluteal phase of the cycle preceding ovulation induction, or before) are associated with easier patient scheduling, greater follicle yield, and overall better clinical results. The use of GnRH antagonists is relatively new to the clinic, but is expected to show similar benefits, with the added advantage of a shorter treatment regimen.

The prolonged administration of GnRH agonists or the administration of GnRH antagonists results in profound suppression of endogenous LH. This situation, while not incompatible with follicle development, does not mimic the natural cycle. In the natural cycle, LH levels show a gradual increase several days before the peak at midcycle.

Several groups have explored the role of LH and chorionic gonadotropin (CG) in ovulation induction and ART. As is well known and recognised in the art, techniques or methods of ovulation induction (OI) are distinct from methods of COH, although both may involve the administration of FSH.

Hillier et al. have demonstrated that very low levels of LH suffice for folliculogenesis[5].

Esposito et al. have studied the role of endogenous LH in ART cycles stimulated with rFSH. They conclude that follicular fluid estradiol levels, oocyte yield, and fertilisation improve when serum LH concentrations are higher than 0.5-1.0 IU/L[6].

WO 00/67778 (Applied Research Systems) discloses the use of LH during the stimulatory phase for inducing folliculogenesis in ovulation induction, particularly to encourage the development of a single dominant follicle.

The European Recombinant Human LH Study Group reports that administration of rhLH (75 and 225 IU/day) for supporting rhFSH-induced follicular development in hypogonadotropic hypogonadal women increases the number and size of follicles[7], with respect to a control group receiving only rhFSH.

Filicori et al. have investigated the role of low doses of hCG, as a surrogate for LH, in controlled ovarian hyperstimulation (Filicori, et al., J. Clin. Endocrin. Metab., 84, 1999, 2659-2663). hCG administration (50 IU hCG/day) was started synchronously with FSH administration and was continued on a daily basis until ovulation was triggered with a bolus of hCG. The numbers of small (<10 mm), medium (10-14 mm) and large (>14 mm) follicles were comparable between a group receiving hCG and a control group receiving FSH alone, however, the cumulative dose of FSH and the duration of FSH stimulation were reduced in the hCG treated group.

Messinis et al. report ovulation induction in anovulatory women (WHO group I) using a regimen that uses daily doses of hMG (75 IU each of FSH and LH) during the stimulatory phase and single or multiple doses of hCG during the luteal phase. The pregnancy rate was found to be significantly increased in patients receiving multiple hCG doses during the luteal phase as compared to a control group that received only a single ovulation inducing/triggering dose of hCG[8].

Proper follicular development is of course essential for successful ART methods. However, there are some cases in which ovulation and fertilisation are achieved, and yet improper implantation of the embryo prevents pregnancy. In other cases, spontaneous abortion (miscarriage) occurs during the first trimester. Both these problems may be associated with conditions in the endometrium, which is quite sensitive to hormone levels. Thus, it can be seen that even once follicular development, ovulation and fertilisation have occurred there is no guarantee of a successful pregnancy and problems with implantation and early miscarriage are often encountered.

In some patients, tendency to abort or failure to implant may eventually be overcome, but to do so requires repeated ART cycles, with consequent negative physiological and psychological effects on the patient. In other patients, these problems represent an essentially permanent stumbling block to pregnancy.

Methods for increasing implantation rates and decreasing early miscarriage rates, particularly in conjunction with COH, are thus highly desirable.

SUMMARY OF THE INVENTION

It is an object of the invention to provide an improved method of administration of gonadotropins for COH, leading to improved implantation rates and decreased miscarriage rates.

It is a further object of the invention to provide a method for increasing pregnancy rates, e.g. by improving implantation rates and/or decreasing miscarriage rates, in patients who are not undergoing COH, for example, in patients following a natural ovulatory cycle or in patients undergoing ovulation induction.

In a first aspect, the invention provides a use of human chorionic gonadotropin (hCG) or an analogue thereof, for the manufacture of a medicament for encouraging implantation and/or decreasing miscarriage rates of an embryo in a human patient, wherein said medicament is administered before ovulation or ovulation triggering.

In a second aspect, the invention provides a use of human chorionic gonadotropin (hCG) or an analogue thereof, for encouraging implantation and/or decreasing miscarriage rates of an embryo in a human patient, wherein said hCG or an analogue thereof is administered before ovulation or ovulation triggering.

In a third aspect, the invention provides a use of human chorionic gonadotropin (hCG), or an analogue thereof, for the manufacture of a medicament for use in conjunction with controlled ovarian hyperstimulation (COH) in human patients using FSH, or an analogue thereof, for aiding implantation and/or decreasing miscarriage rates, wherein the medicament is to be administered starting before the $10^{th}$ day after commencing FSH treatment.

In a fourth aspect, the invention provides a use of human chorionic gonadotropin (hCG), or an analogue thereof, in conjunction with controlled ovarian hyperstimulation (COH) in human patients using FSH, or an analogue thereof, for aiding implantation and/or decreasing miscarriage rates, wherein the hCG or an analogue thereof is to be administered starting before the $10^{th}$ day after commencing FSH treatment.

In a fifth aspect, the invention provides a pharmaceutical composition for use in aiding implantation of an embryo and/or decreasing miscarriage rates, optionally and preferably in conjunction with COH, comprising 25-1000 IU hCG, or an analogue thereof, per dosage.

In a sixth aspect, the invention provides a use of human luteinising hormone (hLH), or an analogue thereof, for the manufacture of a medicament for use in conjunction with controlled ovarian hyperstimulation (COH) in human patients using FSH, or an analogue thereof, for aiding implantation and/or decreasing miscarriage rates, wherein the medicament is to be administered starting before the 10th day after commencing. FSH treatment, preferably between the $3^{rd}$ and the $10^{th}$ day after commencing FSH treatment.

In a seventh aspect, the invention provides a use of human luteinising hormone (hLH), or an analogue thereof, in conjunction with controlled ovarian hyperstimulation (COH) in human patients using FSH, or an analogue thereof, for aiding implantation and/or decreasing miscarriage rates, wherein the LH is to be administered starting before the 10th day after commencing FSH treatment, preferably between the $3^{rd}$ and the $10^{th}$ day after commencing FSH treatment.

In a further aspect, the invention provides a use of LH or an analogue thereof, for the manufacture of a medicament for encouraging implantation and/or decreasing miscarriage rates of an embryo in a human patient, wherein said medicament is administered before ovulation or ovulation triggering.

In a yet further aspect, the invention provides a use of LH or an analogue thereof, for encouraging implantation and/or decreasing miscarriage rates of an embryo in a human patient, wherein said LH or an analogue thereof is administered before ovulation or ovulation triggering.

In a further aspect, the invention provides a pharmaceutical composition for use in aiding implantation of an embryo and/or decreasing miscarriage rates, optionally and preferably in conjunction with COH, comprising 150-1000 IU LH, or an analogue thereof, per dosage.

A further aspect of the invention provides hCG or an analogue thereof or LH or an analogue thereof for use in conjunction with controlled ovarian hyperstimulation (COH) in human patients using FSH, or an analogue thereof, for aiding implantation and/or decreasing miscarriage rates, wherein the hCG or an analogue thereof, or the LH, or an analogue thereof is to be administered starting before the $10^{th}$ day after commencing FSH treatment.

In an alternative embodiment, the invention provides hCG or an analogue thereof or LH or an analogue thereof for encouraging implantation and/or decreasing miscarriage rates of an embryo in a human patient, wherein said hCG or LH or the analogues thereof are administered before ovulation or ovulation triggering.

In a yet further aspect, the present invention provides a method of encouraging implantation and/or decreasing miscarriage rates in a patient, which method is used in conjunction with controlled ovarian hyperstimulation using FSH, or an analogue thereof, which method comprises the administration to the patient of hCG or an analogue thereof, or LH or an analogue thereof, wherein said administration starts before the $10^{th}$ day after commencing FSH treatment.

The present invention also provides a method of encouraging implantation and/or decreasing miscarriage rates in a patient, which method comprises administering to the patient hCG or an analogue thereof, or LH or an analogue thereof, wherein said hCG or LH or the analogues thereof are administered before ovulation or ovulation triggering.

In a further aspect, the invention provides a kit for use in COH comprising 12 or more, preferably 14 or more daily doses of FSH, preferably about 75-200 IU FSH/day, more preferably about 150 IU FSH/day, and 4 to 8, 5 to 8 or 6 to 8 daily doses of hCG, for example 4, 5, 6, 7 or 8 daily doses of hCG, preferably about 25-1000 IU hCG/day, more preferably about 50-100 IU hCG/day.

In a further aspect, the invention provides a kit for aiding implantation of an embryo and/or decreasing miscarriage rates, the kit comprising 4 to 8, 5 to 8 or 6 to 8-daily doses of hCG, for example 4, 5, 6, 7 or 8 daily doses of hCG, at about 25-1000 IU hCG/day, preferably at about 50-100 IU hCG/day. Such kits may or may not be used in conjunction with COH.

Preferably the kits and pharmaceutical compositions of the invention are designed for use in the methods and uses of the invention.

DETAILED DESCRIPTION OF THE INVENTION

Human chorionic gonadotropin (hCG) is a heterodimeric glycosylated peptide hormone which is produced by the placenta during pregnancy. It appears in serum shortly after fertilisation, and acts to maintain the corpus luteum after LH secretion decreases, supporting continued secretion of oestrogens and progesterone and preventing menstruation. Because it is only present at significant levels in the pregnant female, it is not thought to play a significant role in the natural ovulatory cycle. It is known that receptors for LH/hCG exist in the gonads, the uterus, fallopian tubes, placenta and in endometrial and myometrial cells[9]. hCG has the longest half life of the gonadotropins[10].

The inventors have unexpectedly discovered that administration of hCG or an analogue at low doses during the stimulatory phase of ART cycles has a beneficial effect on pregnancy rates, e.g. by aiding or increasing implantation and/or by decreasing miscarriage rates. The expression "low doses" encompasses doses less than the dose conventionally used in a particular patient to trigger follicle maturation, i.e. final follicular maturation, just prior to ovulation ("the follicle (or ovulation) triggering dose"). The follicle/ovulation triggering dose of hCG (usually in the range of 5,000-10,000-IU hCG), will vary on a patient-to-patient basis.

As can be seen from the discussion of standard COH regimens above, the administration of this "high dose" or ovulation triggering dose of hCG is often referred to in the art as the ovulation triggering step, oocyte maturation step or ovulation stimulation step. Such an ovulation stimulation or triggering step or oocyte maturation step involving the administration of a high dose of hCG is however only carried out once adequate follicular development has been achieved during the stimulatory phase of the COH regime, i.e. the phase involving the administration of FSH or an analogue thereof to induce folliculogenesis. A major difference between the methods and uses of the present invention and the prior art regimens is that hCG is administered during the stimulatory phase, i.e. before adequate follicular development has been achieved and before ovulation occurs or is triggered, and is administered at doses below that which induce oocyte maturation and ovulation stimulation, i.e. at doses below the ovulation triggering dose. Such regimens of the present invention give rise to surprising advantages in terms of implantation and miscarriage. Thus, in accordance with the present invention the low doses of hCG are administered in conjunction with COH regimes during the stimulatory phase before adequate follicular development has occurred and before the final high ovulation triggering hCG dose is administered to trigger oocyte maturation and ovulation.

In aspects of the invention where the patients are not undergoing COH low doses of hCG are also administered during the phase of folliculogenesis, and before adequate follicular development has been achieved. Again these doses of hCG are below the ovulation triggering dose. As indicated above, such patients may have a natural ovulatory cycle, in which case the eventual administration of an ovulation triggering dose of hCG will not be necessary. However, some of the patients not undergoing COH which can be treated by the administration of low doses of hCG in accordance with the methods of the invention may not have a natural ovulatory cycle (e.g. those undergoing OI), in which case the administration of an ovulation triggering dose of hCG can be carried out once adequate follicular development is judged to have been achieved.

As mentioned above, the invention also provides the administration of LH rather than hCG in the methods and uses of the invention. The administration of LH is also carried out during the phases of the cycle and follicular development as described herein for hCG.

When hCG is used in the aspects of the invention described herein, the dosage should be in the range of 25-4000 IU hCG/day, preferably 25-1000 IU hCG/day, more preferably 30-1000 or 30-500 IU hCG/day, and particularly preferably 50-100 IU or 75-125 or 75-100 IU hCG/day or 75 or 100 to 500 or 75 or 100 to 1000 IU/day. Such doses are below the ovulation triggering dose and, as described above, are also referred to herein as "low doses" of hCG. If an hCG analogue is used, the equivalent to these hCG doses should be administered.

As indicated above pharmaceutical compositions or kits which may contain such doses of hCG (or doses of LH as described elsewhere herein) for use in the methods and uses of the invention, are also provided.

In aspects of the invention where hCG (or an analogue thereof) is used in conjunction with COH using FSH, or an analogue thereof, administration of hCG (or analogue) should begin before the $10^{th}$ day after starting treatment with FSH, more preferably before the $9^{th}$ day after starting treatment with FSH. Administration of hCG should preferably not be started until at least 3 days after beginning FSH treatment, for example between the 3rd, and 10th day after starting FSH treatment, more preferably not until at least 5 or 6 days after beginning FSH treatment. Particularly preferably, administration of hCG should be started on or about the $7^{th}$ or $8^{th}$ day after commencement of FSH treatment. Thus, hCG is administered during the follicular phase and preferred timepoints for administration of hCG are at or about the mid-follicular stage of the cycle, i.e. at least 5, 6, 7 or 8 days after commencement of FSH treatment.

The administration of hCG in accordance with the present invention may be a single, bolus, in which case it should preferably take place on or about the $7^{th}$ or $8^{th}$ day after FSH treatment is started, and the dosage should preferably comprise 100-1000 IU hCG, more preferably 100-500 IU hCG or 150-600 IU hCG, and particularly preferably about 250 IU hCG. Administration as a single bolus has the advantage of convenience for both the practitioner and the patient.

Alternatively, administration of hCG in accordance with the present invention may be carried out on a daily basis until follicle maturation is triggered or ovulation is induced/triggered with the conventional bolus of hCG. For daily administration, the dosage should be in the range of 25-4000 IU hCG/day, preferably 25-1000 IU hCG/day, more preferably 30-1000 or 30-500 IU hCG/day, most preferably 50-100 IU or 75-125 IU hCG/day or 75-100 or 75 or 100 to 500 or 75 or 100 to 1000 IU/day. A daily regimen that starts on the $7^{th}$ day after commencing FSH treatment, and which uses 50-100 IU hCG/day has been found to be particularly effective. It is also possible to administer hCG on a less frequent basis, for example every two, three, or four days, preferably every two days, until ovulation is triggered. In such regimen doses such as those outlined above may be used, although a dose of 50-200 IU hCG is preferred.

From the above discussion it will be apparent that the hCG (or LH) used in accordance with the present invention is administered starting before ovulation occurs or before ovulation is triggered, e.g. by the ovulation triggering dose of hCG, and is continued until ovulation occurs or is triggered. In all the regimens of the invention, the administration of hCG (or LH) may, if desired, be continued after ovulation if this is thought to be of benefit to the patient.

The timing at which ovulation may be triggered by administration of the "follicle/ovulation triggering dose" of hCG will be well known to a person skilled in ART regimens and can be determined accordingly. In general ovulation is triggered when follicle development is considered adequate for the type of regimen being used. The level of follicle development is generally determined by measuring the size of the follicles (e.g. by ultrasound) and the serum oestradiol ($E_2$) level of the patient. If the regimen in question is COH then because the aim of these methods is multiple follicular development to produce an increased number of mature follicles/oocytes, which are generally fertilised in vitro and reintroduced to the patient, then the timing of the ovulation triggering is likely to be slightly different than if the regimen in question is ovulation induction in which the aim is to produce one, or at the most two, mature follicles which are ovulated and fertilised in vivo. For example in embodiments involving COH regimens ovulation may be triggered with 5000 to 10000, e.g. 10000 IU of hCG when at least two follicles of $\geq 18$ mm in diameter are detected and a serum level of 300 pg/ml oestradiol is attained. Alternatively, in embodiments involving COH regimes, ovulation may be triggered when the largest follicle has reached a mean diameter of at least 18 mm, there are at least two other follicles with a mean diameter of $\geq 16$ mm (i.e. there are at least 3 follicles $\geq 16$ mm and one of these is $\geq 18$ mm) and the oestradiol ($E_2$) level is within an acceptable range for the number of follicles present (approximately 150 pg/ml/mature follicle). For OI, the ovulation triggering dose of hCG may be given when there is at least one follicle $\geq 17$ mm (and it may be withheld if more than three follicles are $\geq 15$ mm).

hCG has a comparatively long half life in the body. For this reason, when multiple doses are used care must be taken that accumulation does not lead to undesirably high levels. It is preferred that serum levels of hCG not rise substantially above 50 IU/L, preferably not above 25 IU/L and most preferably not above about 10 IU/L prior to administration of the ovulation inducing bolus. If hCG levels rise substantially above this level, the result is likely premature luteinisation. The pharmacokinetics of bolus injections of hCG after intramuscular and subcutaneous injection have been reported by Mannaerts et al.[11]

In aspects of the invention where FSH (or an analogue) is used in conjunction with COH techniques or regimens, appropriate doses and administration regimes will be apparent to a person skilled in the art and any appropriate dose and administration regime may be used. For example FSH may be administered daily at a dose of at or about 75 to 250 or 75 to 200 IU/day, preferably at or about 150 to 200 IU/day, most preferably at or about 150 IU/day. In some patients showing a decreased response to FSH it may be desirable to use doses of up to 600 IU/day. A typical regimen is as follows: the patient is started on 150 IU FSH/day. After 3 or 4 days, an ultrasound is performed to evaluate developing follicles. If follicular development is adequate the dose of 150 IU FSH/day may be maintained. If follicular development is inadequate the dose may be increased to 225, 300, 375, 450, 525 or 600 IU FSH/day. Preferably FSH administration continues until the ovulation triggering dose of hCG is given. Ideally, the cumulative dose of FSH should not exceed 6000 IU/cycle.

The terms "improved rate", "encouraging", "aiding", "increased rates", etc., as used herein in connection with an effect on implantation or pregnancy include any measurable improvement or increase in frequency of occurrence of implantation or pregnancy in an individual patient or group of patients treated in accordance with the present invention, for example when compared with the level or frequency of occurrence of implantation or pregnancy in one or more non-treated patients or when compared to the level or frequency of occurrence of implantation or pregnancy in the same patient observed at an earlier time point (e.g. comparison with a "base line" level). For example, in embodiments where hCG or LH is used in conjunction with COH, a relevant comparison is to compare patients treated in accordance with these embodiments to groups of patients having conventional COH or the same patient having conventional COH. Preferably the improvement or increase will be a statistically significant one, preferably with a probability value of $<0.05$. Methods of determining the statistical significance of results are well known and documented in the art and any appropriate method may be used.

The terms "decreased", "decreasing", "reduction", "reducing", etc. as used herein in connection with an effect on miscarriage, refer to any measurable decrease or reduction in the frequency of occurrence of miscarriage in an individual patient or group of patients treated in accordance with the present invention, for example when compared with the frequency of occurrence of miscarriage in one or more non-treated patients or when compared to the level or frequency of occurrence of miscarriage in the same patient observed at an earlier time point (e.g. comparison with a "base line" level). For example, in embodiments where hCG or LH is used in conjunction with COH, a relevant comparison is to compare patients treated in accordance with these embodiments to groups of patients having conventional COH or the same patient having conventional COH. Preferably the decrease will be a statistically significant one, more preferably with a probability value of $<0.05$. Most preferably the uses and methods as described herein in accordance with the present invention result in the prevention of miscarriages. Thus the prevention of miscarriages is also encompassed by these terms.

The use of hCG (or LH) according to the invention may be useful for any patient in which it is believed that infertility may be attributed to early miscarriage or failure to implant, regardless of whether the patient is receiving other exogenous gonadotropins.

Miscarriage is defined as expulsion of the foetus before it is capable of independent survival. Early miscarriage refers to those miscarriages that occur in the first month of foetal development. The methods and uses of the present invention have particular utility in reducing the levels of early miscarriage.

The use of hCG (and indeed LH) according to the invention in conjunction with COH are usually used in conjunction with in vitro fertilisation techniques. However, it is possible that the uses of hCG (and LH) in conjunction with COH as described herein may also be used in conjunction with in vivo fertilisation.

In addition, the use of hCG (and LH) according to the invention may also be in conjunction with in vivo fertilisation in patients who are not undergoing COH, for example regimens involving both natural ovulation and ovulation induction regimens, for example using anti-oestrogens or aromatase inhibitors (i.e. regimens not involving the administration of exogenous gonadotropins). When used in patients receiving no other exogenous gonadotropins, hCG should be administered starting before ovulation is expected to occur in any given cycle, preferably starting on or about the $6^{th}$, $7^{th}$ or $8^{th}$ day after menses. A single bolus may be given (for example at the doses described above for single bolus administration and in particular 100-500 IU hCG), or it may be given on a daily basis (for example at the doses described above for daily administration and in particular at 50-100 IU hCG), or every second day (for example at the doses described above and in particular at 50-200 IU hCG), until ovulation takes place either naturally or, if required, by triggering with an ovulation triggering dose of hCG as described above.

In embodiments of the invention where hCG (or LH) are used in patients not undergoing COH, such patients may alternatively be undergoing OI using exogenous gonadotropins (e.g. exogenous FSH). Appropriate dosages of hCG (or LH) for this use are as described elsewhere herein. Ovulation is triggered at the appropriate time by a high dose of hCG as described above.

Thus, as indicated above, it will be appreciated that as well as the use of hCG (or LH) in accordance with the present invention being advantageous in conjunction with COH regimes using FSH, hCG (or LH) can also be used to improve implantation and/or decrease miscarriage rates of an embryo in a human patient not undergoing a COH regime, but trying to improve their chances of a successful pregnancy. Such patients (or their partners) will generally have experienced fertility problems of some kind, i.e. have some level of infertility or sub-fertility. Alternatively, or additionally, the patients may have no obvious fertility problems in terms of ovulation and fertilisation but may display infertility due to a tendency to early miscarriage and/or failure to implant. Older women e.g. women over 35, where problems with implantation and higher levels of miscarriage are acknowledged, are also good candidates for this treatment. In such patients ovulation may either occur naturally or can be induced by an ovulation induction regime rather than a COH regime, e.g. OI regimes involving aromatase inhibitors, etc. (which stimulate endogenous FSH secretion), or exogenous FSH administration as discussed above. Such OI regimes are standard and well described in the art.

In such uses not involving COH regimes, the timing of administration of the hCG (or LH) is generally calculated from the day of the commencement of menses, although in OI regimes using FSH the timing of administration can be calculated from the day of commencing the FSH treatment. Appropriate timings after mensus or after commencing FSH treatment are as discussed above. As discussed above, the hCG (or LH) is administered starting before ovulation (which may be either natural ovulation or triggered by ovulation triggering doses of hCG), during the follicular phase and preferably in the mid-follicular phase of the cycle, e.g. 5 to 8 days after menses, e.g. 6, 7 or 8 days after menses, or at least 5 or 6 days after beginning FSH treatment, e.g. 5, 6, 7 or 8 days after beginning FSH treatment. Thus, it can be seen that although the treatment regimens in such patients are different from those undergoing COH using FSH, the preferred timing of administration of the hCG (or LH) is similar, i.e. at or around the mid-follicular phase of the cycle.

When LH is used in conjunction with such methods not involving COH the preferred timings of administration are as described above for hCG. Preferably the LH is administered on a daily or semi-daily basis at daily dosages of 125-7000 IU LH or 150-1000 IU LH, more preferably 150-700 or 350-700 IU LH. Other doses which may be used are 10 to 200 IU LH, 10-150 IU LH or 20-100 IU LH/day. A daily dose of 150 IU LH has been shown to be particularly effective in the methods of the invention and is preferred. Administration of LH in accordance with the present invention has been shown to be particularly effective in women who are at least 35 years of age.

LH, FSH and hCG used in the invention may be formulated for administration by any convenient route, generally in association with a pharmaceutically acceptable carrier, diluent or excipient. Appropriate formulations and routes of administration are well known and documented in the art for LH, FSH and hCG and any appropriate route and formulation may be used. Thus, the pharmaceutical compositions of the invention generally contain a pharmaceutically acceptable carrier, diluent or excipient, together with the appropriate active ingredient.

As mentioned above, patients which may benefit from the methods and uses described herein are any patients which suffer some form of infertility or subfertility or any patients which wish to reduce the possibility of miscarriage and/or to reduce problems associated with improper implantation, for example patients who have an increased risk of improper implantation and/or miscarriage, e.g. patients who are at least 35 years old, or patients who have in the past experienced problems with implantation and/or miscarriage. Suitable patients may have a natural ovulation cycle or may be undergoing OI or COH regimens.

Administration of hCG (or LH) according to the invention is useful in those patients being treated with GnRH agonists or antagonists. hCG or LH administration according to the invention is particularly useful in conjunction with IVF or IVF/ICSI. The method results in increased rates of implantation and pregnancies lasting past the first trimester. The use of hCG or LH can lead to implantation even in patients who have previously demonstrated failure in IVF regimens due to problems not associated with ovulation.

The use of hCG or LH according to the invention can be particularly useful in treating patients with low endogenous LH levels, such as patients suffering from hypogonadotrophic hypogonadism.

The use of hCG or LH according to the invention can also be used in patients which have previously exhibited failure to become or remain pregnant using FSH alone, e.g. in standard COH or OI regimens.

Examples of other suitable patient groups are those suffering from PCOD (polycystic ovarian disease), inadequate luteal phase and immunological factors, and patients 35 years old and older ("older patients"). Preferably the patients are not older than 45 years, more preferably not older than 42 years.

The hCG that is used may be from any source, provided it is not contaminated with any materials (particularly other gonadotropins) which will substantially affect its action. Urinary hCG may be used, although it is preferred to use recombinant hCG (rhCG), because of its high purity. Similar conditions apply to the source of hLH for use in the present invention.

Analogues of hCG include all molecules which exert the same physiological, biochemical or biological effects as hCG, and/or bind to the same receptors, as hCG. Luteinising hormone (LH) is known to share some physiological actions with hCG.

Some analogues of hCG include single chain hCG, in which the C-terminus of the β-subunit is fused to the N-terminus of the α-subunit (Sugahara et al., PNAS, 92, 1995, 2041-2045). Other examples of analogues are as is disclosed, for example in European patent no. EP 0 322 226 (Applied Research Systems), WO 92/22568 (University of Medicine & Dentistry of New Jersey), WO 96/05224 (Washington University), WO 90/09800 (Washington University), WO 93/06844 (Washington University), WO 98/43999 (Washington University), WO 99/25849 (Washington University).

hCG may be detected by any appropriate technique for example using radioimmunoassay, as described by Vaitukaitis et al.[12], as well as ELISA assays.[13] The bioactivity of hCG can be measured by any appropriate technique, for example, by the mouse Leydig cell bioassay.[14]

As mentioned above, the use of LH or an analogue thereof is also beneficial during the late stimulatory phase in ART cycles. In COH regimens (i.e. in embodiments when LH is used in conjunction with COH), administration of LH should start before the $10^{th}$ day after starting FSH administration. Because LH has a relatively short half life, administration on a daily or semi-daily basis is preferred. In aspects of the invention where LH is used in conjunction with COH, preferred timings of administration of LH are as described above for hCG. In a most preferred modified COH regimen LH administration is started on or about the $6^{th}$ or $7^{th}$ day after FSH treatment is commenced. Administration of LH should preferably start after the $3^{rd}$ day after commencing FSH treatment. Daily dosages of 125-7000 IU LH or 150-1000 IU LH, more preferably 150-700 or 350-700 IU LH may be administered every day until ovulation is induced. Other doses which may be used are 10 to 200 IU LH, 10-150 IU LH or 20-100 IU LH/day. A daily dose of 150 IU LH has been shown to be particularly effective in the methods of the invention and is preferred.

In aspects of the invention where LH is used in patients who are not undergoing COH similar daily doses can be used.

Analogues of LH include all molecules which exert the same physiological, biochemical or biological effects as LH, and/or bind to the same receptors as LH. hCG is known to share some physiological actions with LH. Some examples of analogues of LH are as disclosed, for example in European patent no. EP 0 322 226 (Applied Research Systems), WO 92/22568 (University of Medicine & Dentistry of New Jersey), WO 96/05224 (Washington University), WO 90/09800

(Washington University), WO 93/06844 (Washington University), WO 98/43999 (Washington University), WO 99/25849 (Washington University), WO 00/61586 (Akxo Nobel).

In embodiments of the invention where FSH is used, it will be understood by one of skill in the art that FSH may be substituted by a biologically active analogue, or by a compound that stimulates endogenous FSH secretion. In this latter class are included aromatase inhibitors, and anti-oestrogens such as tamoxifen and clomiphene citrate (CC). These compounds stimulate endogenous FSH secretion by removing the negative feedback exerted by oestrogen on the hypothalamus (either by antagonising oestrogen receptors, as is the case with CC and tamoxifen, or by greatly decreasing oestrogen concentrations, as is the case with aromatase inhibitors).

A particularly preferred form of FSH for use in conjunction with the use of hCG according to the invention is known as FSH-CTP. This long-acting human FSH is described in WO 93/06844, and has a wild type FSH α-subunit and a β-subunit that consists of the wild type FSH β-subunit fused at its carboxyl terminal to the carboxy terminal peptide (CTP) of the β-subunit of hCG (residues 112-118 to position 145 of the native hCGβ sequence). Other types of FSH analogues include, for example single chain FSH analogues in which the β-subunit is fused to the CTP of hCG, which in turn is fused to FSH α-subunit, as described in WO 96/05224 (single chain FSH-CTP).

As for LH and hCG described above, the FSH used in the methods of the invention can be from any source. Such sources will be well known to a person skilled in the field of ovulation induction and of COH procedures. A urinary preparation of FSH may be used, e.g. hMG which contains FSH and LH activity at a 1:1 ratio. Preferably recombinant FSH will be used (rFSH) because of its high purity.

Human menopausal gonadotropin (hMG) has been used to replace FSH during the stimulatory phase in ovulation induction and COH for IVF. hMG is a relatively crude hormonal extract from the urine of postmenopausal women which contains both FSH and LH activity (ratio 1:1). Non-proprietary hMG may contain as little as 2% of the active hormones and consequently as much as 98% of the protein content may be urinary contaminants. When hMG is used instead of FSH in the methods of the invention, an hCG supplementation as described above, may also prove beneficial, for example for aiding implantation and/or preventing or decreasing miscarriages. hCG administration should be started before the $10^{th}$ day after commencing hMG treatment, more preferably before the $9^{th}$ day after commencing hMG treatment, particularly preferably on or about the $7^{th}$ or $8^{th}$ day after commencing hMG treatment. Administration of hCG should preferably start after the $3^{rd}$ day after commencing hMG treatment. Dosages and dosing regimens are as given for use of hCG in conjunction with FSH. A preferred dose is 150 IU/day, more preferably 50 or 100 IU hCG/day.

hMG can also be used as a source of hLH in the methods of the invention, i.e. hMG can be used as a source of urinary hLH.

The invention will now be described in more detail in the following non-limiting Examples.

EXAMPLES

Example 1

Stimulation Protocol

Control group 1: The first day of menses, the patients were submitted to de-sensitisation by daily injections of decapeptyl (0.1 mg). After 14 days, a sonographic examination was performed and in the absence of cysts, stimulation was started with rFSH (150 to 200 IU/day). After 7 days, follicular growth was checked by sonography and $E_2$ blood concentration was measured. The patients were examined on a daily basis and ovulation was triggered with 10,000 IU of hCG when at least two follicles $\geq$18 mm in diameter were detected and a serum level of 300 pg/mL of $E_2$ was attained. Control group 2: At the time of day 7 in control group 1, control group 2 received hMG (150 IU/day) in addition to the rFSH.

Experimental group: At the time of day 7 in the control group, the experimental group received 50-100 IU of hCG on a daily basis in combination with the rFSH, until ovulation was triggered as above.

The oocytes were fertilised in vitro. Four hours later, they were rinsed and put into culture medium (ISM1). After 20 hrs, fertilisation was checked and the embryos remained in the same medium until 48 hrs. They were then transferred into a second culture medium (ISM2). The 2 best embryos were then transferred to patients and the remaining were cultured until blastocyst formation was reached (day 5-6).

Results

The results are summarised in Tables 1, 2 and 3. Tables 1 and 2 show results comparing control group 1 (rFSH alone) with the experimental group. (RFSH+hCG). Table 3 shows results comparing control group 2 (rFSH+hMG) with the experimental group (rFSH+hCG).

There was no difference in the lengths of the stimulation periods. $E_2$ levels were increased in the group receiving hCG. The transfer rates were similar in both groups: 92% with hCG Vs 86% in the control group (p=0.1). Blastocyst formation from the supernumerary embryos was not different between the 2 groups ($^{185}/_{411}$=45% with hCG Vs $^{292}/_{627}$=46.5% control, p=0.622). Implantation rates (24.5% hCG Vs 14.6% control, p=0.0134) as well as pregnancy rates per transfer (37.5% hCG Vs 23.6% control, p=0.0246) were increased in the hCG group, yielding a mean number of 1.9 embryo per transfer.

TABLE 1

| hCG low dose in stimulation with rFSH | | |
|---|---|---|
| | +hCG | No hCG |
| No. of patients | 96 | 127 |
| Rank (age) | 2.2 (32.8 ± 4.1) | 1.5 (32.1 ± 4.5) |
| | | (p = 0.1068) |
| Transfers | 89 (92%) | 109 (86%) |
| Stimulation (days) | 11.7 | 12.3 |
| Oocytes recovered | 10 | 9.7 |
| Embryos (m) | 6.2 (62%) | 5.4 (56%) |
| Implantations | 43/175 (24.5%) | 30/206 (14.6%) |
| | | (p = 0.0134) |
| Embryo/transfer | 1.97 | 1.89 |
| Pregnancies | 36/96 (37.5%) | 30/127 (23.6%) |
| | | (p = 0.0246) |
| Blastocysts | 185/411 (45%) | 292/627 (46.5%) |
| | | (p = 0.6221) |

TABLE 2

| hCG low dose in stimulation with rFSH | | | |
|---|---|---|---|
| | +hCG | No hCG | Total |
| Pregnancies | 109 | 230 | 339 |
| Ectopics | 2 | 6 | 8 (2.4%) (p = 0.95) |
| Miscarriages | 8 (7.3%) | 36 (15.6%) | 44 (13%) (p = 0.03) |
| Total miscarriages + ectopics | 10 (9.17) | 42 (18.3) | 52 (15.7) (p = 0.03) |

TABLE 3 hCG low dose in stimulation with rFSH Vs hMG

|  | FSH +hCG | hMG |  |
|---|---|---|---|
| Pregnancies | 109 | 76 |  |
| Ectopics | 2 | 2 |  |
| Miscarriages | 8 | 13 | (p = 0.049) |
| Total miscarriages + ectopics | 10 | 15 | (p = 0.049) |

Example 2

The following study compared the pregnancy outcome of patients treated in COH using FSH alone, with those treated using FSH plus LH starting on day 6.

Following a negative quantitative serum pregnancy test, eligible participants underwent pituitary desensitisation using the gonadotrophin releasing-hormone agonist (GnRH-a), Lupron®, starting 7 to 8 days after estimated ovulation at a dose of 0.5 mg daily until desensitisation was established by a serum estradiol (E2) level of <75 pg/mL. At that time, treatment with recombinant human FSH at a starting dose of 225 IU subcutaneous per day was initiated. This dose continued for the first 5 treatment days at which time the dose could be increased by 75 to 150 IU/day every 2 to 3 days if the patient's ovarian response was judged to be slow. The maximum dose of FSH allowed was 450 IU/day and the maximum cumulative dose was not to exceed 6,000 IU per cycle. For those patients randomised to receive FSH plus r-hLH, r-hLH treatment was initiated at a dose of 150 IU per day on stimulation Day 6. The dose of r-hLH was not to be modified. After achieving down-regulation, Lupron treatment continued throughout the stimulation cycle at a dose of 0.25 mg daily until administration of hCG. Estradiol levels and ultrasound measurements were assessed throughout the stimulation cycle to determine patient response to treatment. The administration of FSH or FSH plus r-hLH continued daily until follicular development was considered adequate. The criteria for hCG administration (for ovulation triggering) was met when the largest follicle reached a mean diameter ≧18 mm and at least two other follicles had a mean diameter of ≧16 mm. The patients also needed an E2 level within the investigator's acceptable range for the number of follicles present (approximately 150 pg/ml/mature follicle). At that time, the patient received a single IM injection of 10,000 USP units of hCG for the final stage of follicular maturation. Oocytes were recovered vaginally under ultrasound monitoring 34 to 36 hours after the administration of hCG in accordance with the usual practice of the investigational site. Intracytoplasmic sperm injection (ICSI) was then performed according to the standard procedures at each site. Up to 3 embryos could be replaced 2 to 3 days after ovum pick-up. Luteal phase support with natural progesterone in oil was provided for all patients who received hCG starting on the evening of oocyte retrieval and continuing for a minimum of 7 days; the investigator could then choose to use progesterone suppositories. The total duration of luteal phase support was at the discretion of the investigator.

A blood sample for serum β-hCG level was collected on day 15 to 17 after hCG injection for all patients who underwent embryo transfer. If the results were positive (biochemical pregnancy), the test was repeated 2 to 7 days later.

A post-treatment visit including general physical examination and clinical laboratory testing was conducted in all patients 15 to 17 days following hCG administration (when the patient returned for pregnancy testing) or within one week of onset of menses. For all patients who became pregnant, an ultrasound scan was performed 35 to 42 days after hCG administration and the number of fetal sacs and fetal heart activity was recorded ("clinical pregnancy"). If clinical pregnancy occurred, women were followed to determine pregnancy outcome.

The data were analysed dividing the patients into those aged 35 years and older ("older patients"), and those aged less than 35 years. The clinical pregnancy data are shown in Table 4. The treatment of FSH+LH is clearly better in pregnancy outcome in patients aged 35 years and older (48.8% with FSH+LH VS 21.6% with FSH alone).

TABLE 4

Pregnancy data for patients treated with FSH alone versus patients treated with FSH + LH (LH starting on day 6)

| | FSH + LH | | | FSH | | |
|---|---|---|---|---|---|---|
| | <35 | ≧35 | Overall | <35 | ≧35 | Overall |
| | Number of patients (N) | | | | | |
| | 103 | 41 | 144 | 107 | 37 | 144 |
| Clinical pregnancies (%) | 46 (44.7%) | 20 (48.8%) | 66 (45.8%) | 48 (44.9%) | 8 (21.6%) | 56 (38.9%) |

REFERENCES

[1] Healy et al.; Lancet 343 1994; 1539-1544
[2] for example, a conventional technique is described in EP 0 170 502 (Serono Laboratories, Inc.)
[3] Filicori, M.; J. Clin. Endocrinol. Metab. 81 1996; 2413-6
[4] Filicori, M. et al; Fertil. Steril. 65 1996; 387-93
[5] Hillier et al; Horm. Res. 43 1995; 216-223
[6] Esposito et al.; Fertility & Sterility 75 2001; 519-524
[7] The European Recombinant Human LH Study Group; J. Clin. Endocrinol. Metab. 83 1998; 1507-1514
[8] Messinis et al.; Fertility & Sterility 50-1988; 31-35
[9] Lei et al.; J. Clin. Endocrinol. Metab. 75 1992; 651-659
[10] Bennett et al.; Pharmacol. Rev. 30 1979; 247-292
[11] Mannaerts et al.; Human Reproduction 13 1998; 1461-1464
[12] Vaitukaitis et al.; Am. J. Obstet. Gynecol. 113 1972; 751; Clin. Chem. 31 1985; 1749
[13] Tyrey et al.; Obstet. Gynecol. Clin. North Am. 15 1988; 457
[14] Robertson, W. R. and Binden, S. P; The in vitro bioassay of peptide hormones. In Hutton, J. C. and Siddle, K. (eds), Peptide Hormones; a Practical Approach. IRL Press, Oxford (1990).

The invention claimed is:

1. A method for aiding/encouraging implantation and/or decreasing miscarriage rates of an embryo in a human patient, comprising administering human luteinising hormone (hLH) during controlled ovarian hyperstimulation (COH) in a human patient in need thereof, while continuing administration of FSH, wherein the hLH is administered starting between the $3^{rd}$ and $10^{th}$ day after commencing treatment with FSH, to aid/encourage implantation and/or decrease miscarriage rates of an embryo in the human patient.

2. The method according to claim 1, wherein the hLH is administered at a dosage of 125-7000 IU hLH/day.

3. The method according to claim 1, wherein the hLH is administered starting between the $3^{rd}$ and $8^{th}$ day after commencing treatment with FSH.

4. The method according to claim 3, wherein the human patient is at least 35 years of age.

5. The method according to claim 1, wherein the hLH is recombinant hLH.

6. The method according to claim 1, wherein the hLH is urinary hLH.

* * * * *